(12) United States Patent
Kennedy et al.

(10) Patent No.: US 11,872,210 B2
(45) Date of Patent: Jan. 16, 2024

(54) THIOL ISOMERASES INHIBITORS AND USE THEREOF

(71) Applicant: WESTERN NEW ENGLAND UNIVERSITY, Springfield, MA (US)

(72) Inventors: Daniel Kennedy, Longmeadow, MA (US); Jonathan Gibbins, Reading (GB); Lisa-Marie Holbrook, Basingstoke (GB)

(73) Assignee: WESTERN NEW ENGLAND UNIVERSITY, Springfield, MA (US)

( * ) Notice: Subject to any disclaimer, the term of this patent is extended or adjusted under 35 U.S.C. 154(b) by 58 days.

(21) Appl. No.: 16/480,844

(22) PCT Filed: Jan. 29, 2018

(86) PCT No.: PCT/US2018/015694
§ 371 (c)(1),
(2) Date: Jul. 25, 2019

(87) PCT Pub. No.: WO2018/140858
PCT Pub. Date: Aug. 2, 2018

(65) Prior Publication Data
US 2021/0008032 A1    Jan. 14, 2021

Related U.S. Application Data

(60) Provisional application No. 62/451,858, filed on Jan. 30, 2017.

(51) Int. Cl.
*A61K 31/404* (2006.01)
*A61K 9/20* (2006.01)
*A61K 9/48* (2006.01)
*A61K 45/06* (2006.01)

(52) U.S. Cl.
CPC .............. *A61K 31/404* (2013.01); *A61K 9/20* (2013.01); *A61K 9/48* (2013.01); *A61K 45/06* (2013.01)

(58) Field of Classification Search
CPC .................................................. A61K 31/404
See application file for complete search history.

(56) References Cited

U.S. PATENT DOCUMENTS

| | | |
|---|---|---|
| 4,496,572 A | 1/1985 | Cross et al. |
| 4,590,200 A | 5/1986 | Cross et al. |
| 4,859,692 A | 8/1989 | Bernstein et al. |
| 4,985,465 A | 1/1991 | Hendler |
| 5,294,636 A | 3/1994 | Edwards et al. |
| 5,319,097 A | 6/1994 | Holohan et al. |
| 5,482,963 A | 1/1996 | Holohan et al. |
| 5,565,473 A | 10/1996 | Belley et al. |
| 5,583,152 A | 12/1996 | Bernstein et al. |
| 5,612,367 A | 3/1997 | Timko et al. |
| 6,143,775 A | 11/2000 | Holohan et al. |
| 6,333,361 B1 | 12/2001 | Corvari et al. |
| 6,399,104 B1 | 6/2002 | Creekmore et al. |
| 8,058,243 B2 | 11/2011 | Tyers et al. |
| 8,809,283 B2 | 8/2014 | Arbiser |
| 2006/0145209 A1 | 7/2006 | Han |
| 2008/0004321 A1* | 1/2008 | Aicher ................. C07D 213/70 514/354 |
| 2008/0161324 A1 | 7/2008 | Johansen et al. |
| 2009/0142277 A1 | 6/2009 | Osbakken et al. |
| 2009/0233963 A1 | 9/2009 | Rabinovitch et al. |
| 2011/0098333 A1 | 4/2011 | Kim |
| 2014/0275162 A1 | 9/2014 | Yang |
| 2015/0038530 A1 | 2/2015 | Abraham et al. |
| 2016/0058748 A1* | 3/2016 | Sugamata ............... A61P 25/04 514/311 |
| 2016/0145209 A1* | 5/2016 | Flaumenhaft ........... A61P 35/00 514/330 |

FOREIGN PATENT DOCUMENTS

| | | |
|---|---|---|
| CN | 103505731 A | 1/2014 |
| JP | 2016175866 A | 10/2016 |
| WO | 200238545 A2 | 5/2002 |
| WO | 2008083992 A1 | 7/2008 |
| WO | 2013055674 A1 | 4/2013 |
| WO | 2014164285 A2 | 10/2014 |
| WO | 2014175253 A1 | 10/2014 |
| WO | 2015079254 A1 | 6/2015 |
| WO | 2016118639 A1 | 7/2016 |
| WO | 2014175253 A1 | 2/2017 |

OTHER PUBLICATIONS

Bundgaard, Design of Prodrugs, p. 1, 1985.*
Banker et al., Prodrugs, Modern Pharmaceutics, Third Edition, Revised and Expanded, pp. 451 and 596 (1996).*
Silverman, Prodrugs and Drug Delivery Systems, The Organic Chemistry of Drug Design and Drug Action, pp. 352-399, 1992.*
Wolff, Some consideration for prodrug design, Burger's Medicinal Chemistry and Drug Discovery, 5th Edition, vol. 1: Principles and Practice, pp. 975-977, 1995.*
Ulrich, Crystallization, Kirk-Othmer Encyclopedia of Chemical Technology, pp. 1-7, 2002.*
Vippagunta et al., Crystalline Solids, Advanced Drug Delivery Reviews 48 (2001), pp. 3-26.*
Bosseray et al., PubMed Abstract (Pathol Biol (Paris) 50(8): 483-92), 2002.*

(Continued)

*Primary Examiner* — Deepak R Rao
(74) *Attorney, Agent, or Firm* — CANTOR COLBURN LLP

(57) ABSTRACT

Disclosed herein is a method of administering to a patient in need thereof a therapeutically effective amount of an extracellular thiol isomerase inhibitor compound to treat or prevent a disease or condition influenced by the activity of one or more extracellular thiol isomerases (e.g. protein disulfide isomerase, ERp5, ERp57, ERp72 and thioredoxin). The disease or condition includes arterial thrombosis, venous thrombosis, a thrombotic disease, a cancer, an infectious disease, a viral disease, an immune disorder, inflammation, a neurologic disease, and a neurodegenerative disorder.

11 Claims, 4 Drawing Sheets

(56) References Cited

OTHER PUBLICATIONS

Razonable et al., PubMed Abstract (Herpes 10(3): 60-5), 2003.*
Goff, PubMed Abstract (J Gene Med 3(6): 517-28), 2001.*
Douglas, Jr., Introduction to Viral Diseases, Cecil Textbook of Medicine, 20th Edition, vol. 2, pp. 1739-1747 (1996).*
Simone, Oncology: Introduction, Cecil Textbook of Medicine, 20th Edition, vol. 1, pp. 1004-1010, 1996.*
Acute Leukemia, Merck Manual (Online Edition) 6 pages, pp. 1-6 (2013).*
Pearce et al., Failure modes in anticancer drug discovery and development, Cancer Drug Design and Discovery Edited by Stephen Neidle, Chapter 18, pp. 424-435 (2008).*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Newman et al., Solid form changes during drug development: good, bad and ugly case studies, AAPS Open, 2:2 (2016), 11 pages.*
Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*
Schain et al., Evidence of a pathophysiological role of cysteinal leukotrienes in classical Hodgkin lymphoma, Int. J. Cancer. 123. pp. 2285-2293 (2008).*
Brussel, Van J.P. et al.; "Identification of multidrug resistance-associated protein 1 and glutathione as multidrug resistance mechanisms in human prostate cancer cells: chemosensitization with leukotriene D4 antagonists and buthionine sulfoximine"; BJU International, vol. 93; 2004; pp. 1333-1338.
Gumireddy, Kiranmai et al.; "In Vivo Selection for Metastasis Promoting Genes in the Mouse"; PNAS, vol. 104, No. 16; Apr. 17, 2007; pp. 6696-6701.
Gunning, William T. et al.; "Chemoprevention by lipoxygenase and leukotriene pathway inhibitors of vinyl carbamate-induced lung tumors in mice"; Cancer Research, vol. 62; Aug. 1, 2012; pp. 4199-4201.
He, Ningning et al.; "Somatic mutation patters and compound response in cancers"; BMB Reports, vol. 46, Issue 2; 2013; pp. 97-102.
International Search Report for International Application No. PCT/US2018/15694, International Filing Date Jan. 29, 2018, dated Jun. 27, 2018, 5 pages.
Jasuja, Reema et al.; "Protein Disulfide Isomerase Inhibitors Constitute a New Class of Antithrombotic Agents" The Journal of Clinical Investigation, vol. 122, No. 6: Jun. 2012; pp. 2104-2113.
Kahnt, Astrid Stefanie et al.; "Cysteinyl Leukotriene-receptor-1 Antagonists Interfere with PGE2 Synthesis by Inhibiting mPGES-1 Activity"; Biochemical Pharmacology, vol. 86; 2013; pp. 286-296.
Miller, Susanne C. et al.; "Identification of Known Drugs that Act as Inhibitors of NF-κB Signaling and their Mechanism of Action"; Biochemical Pharmacology, vol. 79; 2010; pp. 1272-1280.
Nair, Divya Gopalakrishnan et al.; "Interactions of Some Commonly Used Drugs with Human α-Thrombin" Journal of Biomolecular Structure and Dynamics, vol. 33, No. 5; 2015; pp. 1008-1015.
Orlandi, Palmer A.; "Protein-disulfide Isomerase-mediated Reduction of the A Subunit of Cholera Toxin in a Human Intestinal Cell Line"; The Journal of Biological Chemistry, vol. 272, No. 7: Feb. 14, 1997; pp. 4591-4599.
Parakh, Sonam et al.; "Novel Roles for Protein Disulphide Isomerase in Disease States: a Double Edged Sword?"; Frontiers in Cell and Developmental Biology, vol. 3, Article 30; May 21, 2015; pp. 1-11.
Roy, Upal et al.; "Montelukast Is a Potent and Durable Inhibitor of Multidrug Resistance Protein 2-Mediated Efflux of Taxol and Saquinavir"; Biological & Pharmaceutical Bulletin; vol. 32, No. 12; 2009; pp. 2002-2009.

Wittkowsky, Ann K. et al.; "Frequency of Concurrent Use of Warfarin with Potentially Interacting Drugs"; Pharmacotherapy, vol. 24, No. 12; 2004; pp. 1668-1674.
Written Opinion for International Application No. PCT/US2018/15694, International Filing Date Jan. 29, 2018, dated Jun. 27, 2018, 11 pages.
Xu, Shili et al.; "Protein Disulfide Isomerase: A Promising Target for Cancer Therapy"; Drug Discovery Today, vol. 19, No. 3: Mar. 2014; pp. 222-240.
Back, Magnus et al.; "Anti-inflammatory therapies for atherosclerosis"; Nat. Re. Cardiol., 12, p. 199-211 (2015).
Dong-Min, Xu et al.; "Antioxidative effects of cysteinyl leukotriene receptor antagonists montelukast & HAMI 3379 on ischemic injury in rat cortical neurons in vitro"; Database Medline, US National Library of Medicine, May 2014, XP002801650, p. 1-2.
Henry, Abigail et al.; "identifying Novel Small Molecule Inhibitors of ERp57 through a Medium Sized High Throughput Screen" American Association of Colleges of Pharmacy Annual Meeting—Boston, Massachusetts—Jul. 2018.
Holbrook, L. et al.; "The Identification & characterization of a novel, selective ERp57 inhibitor that modulates platelet function through integrin allbβ3 outside-in signalling dep & indep mech"; ICMR V 1: p. 1255. doi:10.1002/rth2.12012 2017.
Holbrook, L. et al.; "The anti-asthma therapeutic zafirlukast is a broad spectrum thiol isomerase inhibitor that inhibits platelet function"; ICMR, Research and Practice in Thrombosis and Haemostasis. (Abstract Jul. 2017 first published Jun. 23, 2017) vol. 1: p. 1272. doi:10.1002/rth2.12012.
Holbrook, L. et al.; "Third EUPLAN Conference Sep. 21-23, 2016—Abstract Submission for Oral Presentation" 1 page.
Holbrook, L. et al.; "UK Platelet Meeting Sep. 15-16, 2015—abstract for Oral presentation". 1 page.
Long M. Alissa et al; "Exploring the Role of the Thiol Isomerase ERp57 In Cancer Progression Using Novel Small Molecule Inhibitors"; Jul. 2016 2016 AACP.
Merritt, Jennifer A. et al.; "Exploring Thiol Isomerase Enzymes in Cancer Progression" American Journal of Pharmaceutical Education: vol. 84, Issue 6, Article 8221, (Jul. 2020).
Pantos, Megan M. et al.; "Exploring Montelukast as a Potential Broad Spectrum Thiol Isomerase inhibitor"; American Journal of Pharmaceutical Education: vol. 83, Issue 5, Article 7654. (Jul. 2019).
Pantos, Megan M. et al.; "Exploring Zaflriukast for the Inhibition of Platelets, Cancer Cell Growth and Factor Xa Generation"; American Journal of Pharmaceutical Education: vol. 84, Issue 6, Article 8221, Jul. 2020.
Polukort, Stephanie H. et al; "Inhibition of protein disulfide isomerases suppresses mast cell activation and function during food allergy"; American Journal of Pharm Education vol. 82, Issue 5, Article 7158. (Jul. 21-25, 2018).
Riccioni, G. et al.; "Antileukotrlene Drugs: Clinical Application, Effectiveness and Safety"; Current Medicinal Chemistry, 2007, 14, p. 1966-1977.
Said, Mahmoud M. et al.; "The anti-inflammatory effect of montelukast, a cysteinyl leukotriene receptor-1 antagonist, agains estradiol-induced nonbacterial inflammation in the rat prostate"; Naunyn-Schmiedeberg's Arch Pharmacol, 2017, 390: p. 197-205.
Savari, Sayeh et al.; "CysLT1R Antagonists Inhibit Tumor Growth in a Xenograft Model of Colon Cancer"; PLOS ONE, Sep. 2013, 8:9, p. 1-14.
Supplementary European Search Report for EP18745381, International Filing Date Jan. 29, 2018, dated Jan. 27, 2021, 12 pages.
Verbetsky, Christina A. et al.; "Zafirlukast Inhibits Cancer Cell Growth Via Inhibition of Thiol Isomerase Activity"; American Journal of Pharmaceutical Education vol. 82, Issue 5, Article 7153, (Jul. 2018).
Verbetsky, Christina, A. et al.; "Exploring The Effect Of A PDI Inhibitor On Cellular Model Of Cancer Induced Thrombosis After Chemotherapy"; American Journal of Pharmaceutical Education: vol. 83, Issue 5, Article 7654. (Jul. 2019).

(56) References Cited

OTHER PUBLICATIONS

Zhao, Rui et al.; "Montelukast, a cysteinyl leukotriene receptor-1 antagonist, attenuates chronic brain injury after focal cerebral ischaemia in mice and rats"; Journal of Pharmacy and Pharmacology, 2011, 63: p. 550-557.

Brown, Milton L.; "Comparative molecular field analysis and synthetic validation of a hydroxyamide-propofol binding and functional block of neuronal voltage-dependent sodium channels"; Bioorganic & Medicinal Chemistry, vol. 17, Is 19. 2009. p. 7056-7063.

Bushelev, S.N.; "Molecular-orbital analysis of electronic structure & the construction of structure-activity and structure-toxicity quantitative relations for water-soluble ionol derivatives"; Doklady Akademii Nauk SSSR, VI. 280, Is. 5. 1985. pp. 1166-1169.

Capra, V. et al.; "Cystelnyl-leukotrlene Receptor Antagonists: Present Situation and Future Opportunities"; Current Medicinal Chemistry, vol. 13, Issue 26. 2006. pp. 3213-3226.

Elam, Christopher et al.; "Discovery of novel SERCA inhibitors by virlual screening of a large compound library"; European Journai of Medicinal Chemistry, vol. 46, Issue 5. 2011. pp. 1512-1523.

Erokhin, V.N. et al.; "Effect of antioxidant β-(4-hydroxy-3,5-ditertbutylphenyl) Propionic acid (phenosan) on the development of malignant neoplasms"; Biology Bulletin, vol. 34, Issue 5. 2007. pp. 485-491.

Erokhin, V.N. et al.; "Effect of synthetic and natural antioxidants on the emergence and development of malignant tumors"; Vestnik KazanskogoTeknologicheskogo Universiteta, vol. 18, Issue 1. 2015. pp. 367-370.

Fuji, S; "PAI-1 in Thrombosis and Arteriosclerosis"; Fibrinolysis & Proteolysis, vol. 11, Suppl. 2, Update In Thrombolysis, 1997. pp. 137-140.

Kezell, T. et al.; "Effect of combination of zafirlukast and quercetin on baroreflex sensitivity and endothelin production in rats with myocardial infarction"; Int. Journal of Clinical Pharmacology and Therapeutics, V. 48(5), p. 335-341.

Khan et al.; "Discovery of a Small Molecule PDI Inhibitor That Inhibits Reduction of HIV-1 Envelope Glycoprotein gp120"; ACS Chemical Biology, vol. 6, No. 3. Mar. 2011.

Kirillov, V.N. et al.; "Influence of fenozan on nitrosodimethylamine-induced carcinogenesis in rat kidneys"; Eksperimental'naya Onkologiya, vol. 10, Issue 5. 1988. pp. 23-26.

Kirso, U. et al.; "Effects of antioxidants on the carcinogenic and mutagenic activity of benzo[a]pyrene"; Voprosy Onkologii, vol. 3, Issue 4. 1985. pp. 70-75.

Mikhailov, V F et al.; "Signal function of the reactive O2 species in regulatory networks of the cell reaction to damaging effects: contribution of radiosensitivity & genome instability"; Radiatsionnaia biologila, radioecologiia, V 43, I 1. 2003. p 5-18.

Mil', E.M. et al.; "The influence of the antioxidant phenoxan and low dose radiation on the level of p53 and Bcl-2 proteins in mice of different lines"; Radiatsionnaya Biologiya, Radioekologiya, vol. 50, Issue 1. 2010. pp. 58-64.

Pal'Mina, N.P. et al.; "Modification of Chemotherapeutic Activity in Adriablastine with the Synthetic Antioxidant in Low Doses"; Bulletin of Experimental Biology and Medicine, vol. 135-136, Issue Suppl. 1. 2003. pp. 52-53.

Riccioni, G. et al.; "Antileukotriene Drugs: Clinical Application, Effectiveness and Safety"; Current Medicinal Chemistry, vol. 14, Issue 18. 2007. pp. 1966-1977.

Sun, Yue-Li et al.; "Zafirlukast Antagonizes ATP-binding Cassette Subfamily G Member-Mediated Multidrug Resistance"; Anti-Cancer Drugs, vol. 23, Issue 8; 2012. pp. 865-873.

Tan, Zhi-Jie et al.; "Preventive Effects of Zafirlukast on Colorectal Cancer induced by Azoxymethane in Rats"; Zhongguo Linchuang Yanjiu, vol. 23, Issue 10; 2010. pp. 847-849.

Vekshina, O.M. et al.; "Changes in the structure & functions of membranes in erythrocytes & Ehrlich ascites carcinoma cells under the influence of a new generation hybrid antioxidant IKhFAN-10"; Bulletin of Exp Bio & Medicine V. 143 I. 4. 2007. p. 426-430.

Wang, Haidong et al.; "Elucidation of a CGP7930 in vitro metabolite by liquid chromatography/electrospray ionization quadrupole time-of-flight tandem mass spectrometry"; Rapid Communications in Mass Spectrometry, vol. 30, Issue 4. 2016. pp. 491-496.

Ingelsson et al., Nationwide cohort study of the leukotriene receptor antagonist montelukast and incident or recurrent cardiovascular disease, J. Allergy Clin. Immunol. 2012; 129(3), 702-707.

The Protest filed in the corresponding Canadian Application CA3052071A, (Feb. 28, 2023).

U. Klotz, The Pharmacological Profile and Clinical, Arzneimittelforschung 2012; 62: 53-58.

* cited by examiner

THIOL ISOMERASES INHIBITORS AND USE THEREOF

CROSS-REFERENCE TO RELATED APPLICATIONS

This Application is a U.S. National Stage Application of International Application No. PCT/2018/015694, filed Jan. 29, 2018, which claims the benefit of U.S. Provisional Application No. 62/451,858, filed Jan. 30, 2017, each of which is incorporated by reference in its entirety.

BACKGROUND

Thiol isomerases are members of a large family of disulfide oxidoreductases, which catalyze the posttranslational disulfide exchange necessary for the proper folding of newly synthesized proteins. Approximately twenty members of a large family of thiol isomerase/disulfide oxidoreductases exist in humans with a domain composition of thiol isomerases is a-b-b'-a'. These thiol isomerases are generally capable of oxidation reduction and isomerization reactions and are often found in the endoplasmic reticulum where they catalyze the proper folding of newly translated proteins.

Additionally, some thiol isomerases such as protein disulfide isomerase (PDI), ERp5, ERp57, ERp72 and thioredoxin (TRX) have recently been discovered to perform extracellular functions. These five thiol isomerases, henceforth referred to as extracellular thiol isomerases, are secreted by cells such as platelets and reattach to the plasma membrane, where they function as extracellular oxidoreductases. Extracellular thiol isomerases have also been identified on the surface of endothelial cells and to play a role in the activation of thrombus formation and fibrin formation, as well as in platelet aggregation, granule secretion, fibrinogen binding, and calcium mobilization. Of these enzymes, the role of PDI in thrombus formation is the most-well studied and understood, while ERp5, ERp57 and ERp72 are also known to be required.

Tools for investigating thiol isomerases have mainly comprised of antibodies which have limitations. There remains a need in the art for pharmaceuticals, including small molecules, directed against these thiol isomerases that would offer a novel approach to antithrombotic therapy.

In addition, PDI family members are upregulated in many distinct cancer types, including ovarian, prostate, lung, melanoma, lymphoma and glioma, while inhibition of PDI is cytotoxic in ovarian cancer cell lines. These enzymes are thought to have polyfunctional involvement in the oncogenesis of cancer, where they play roles in the oncogene activation, avoidance of apoptosis, secretion of major histocompatibility complex class I-related A protein (MICA), and the resistance to chemotherapeutic agents.

There further remains a need in the art for pharmaceuticals, including small molecules, directed against these thiol isomerases to treat cancer and other disease-associated processes in which extracellular thiol isomerases are implicated.

There is also a need in the art for the development of pharmaceuticals to target extracellular thiol isomerases, both selectively and broadly, for preventing and treating the development or progression of diseases and conditions involving extracellular thiol isomerases.

SUMMARY

Disclosed herein is a method comprising administering to a patient in need thereof a therapeutically effective amount of an extracellular thiol isomerase inhibitor compound to treat or prevent a disease or condition influenced by the activity of one or more extracellular thiol isomerases, wherein the extracellular thiol isomerase inhibitor compound is zafirlukast, montelukast, CGP-13501, CGP-7930, alosetron, balsalazide, benserazide, butaclamol, leva-dopa, mesalazine, oxcarbazepine, a pharmaceutically acceptable salt, prodrug, and/or a solid state form thereof.

In another embodiment, a method for preventing or treating thrombosis, a thrombotic disease, platelet aggregation, fibrin generation, or a combination thereof in a patient comprises administering to the patient in need thereof a therapeutically effective amount of zafirlukast.

In yet another embodiment, a method for inhibiting a thiol isomerase of the extracellular thiol isomerases in a cell comprises contacting the cell with an effective amount of zafirlukast, montelukast, CGP-13501, CGP-7930, alosetron, balsalazide, benserazide, butaclamol, leva-dopa, mesalazine, oxcarbazepine, a pharmaceutically acceptable salt, prodrug, and/or a solid state form thereof.

The above described and other features are exemplified by the following figures and detailed description.

In general, the disclosure may alternately comprise, consist of, or consist essentially of, any appropriate components herein disclosed. The disclosure may additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

DRAWINGS

Referring now to the figures, which are exemplary embodiments and not to be considered limiting:

DETAILED DESCRIPTION

Figure 1:
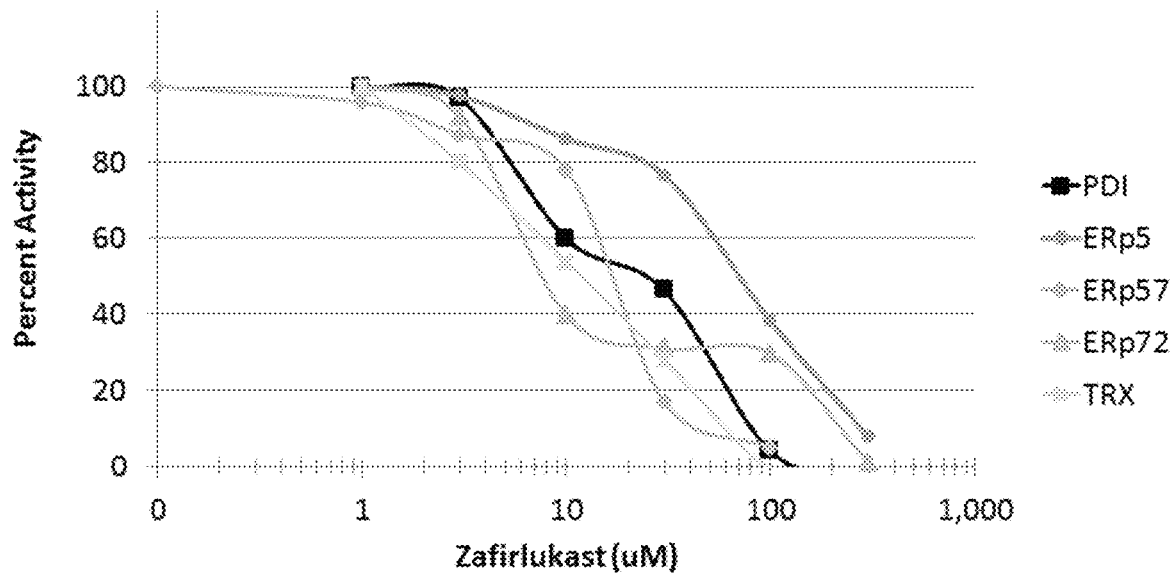
FIG. 1 illustrates data on the inhibition of various thiol isomerases by zafirlukast in an in vitro enzymatic assay.

Disclosed herein are thiol isomerase inhibitors and their therapeutic use in the prevention or treatment of the development or progression of a disease or condition involving one or more of the extracellular thiol isomerases.

In an embodiment, a method of inhibiting one or more of the extracellular thiol isomerases in a patient in need thereof for the treatment or prevention of a disease or condition influenced by the activity of one or more of the extracellular thiol isomerases, or for inhibiting a process influenced by the activity of one or more of the extracellular thiol isomerases, the method comprises administering to the patient a therapeutically effective amount of an extracellular thiol isomerases inhibitor compound or composition comprising an extracellular thiol isomerase inhibitor compound as disclosed herein. In certain embodiments, the disease or condition is thrombosis, a thrombotic disease, an infectious disease including human immunodeficiency virus (HIV), a cancer, inflammation, or a combination thereof, as described herein.

Extracellular Thiol Isomerases

As used herein, "extracellular thiol isomerase" includes at least protein disulfide isomerase (PDI), thioredoxin (TRX), and the following endoplasmic reticulum resident proteins: ERp5, ERp57, and ERp72.

PDI is a 508 amino acid protein that has an important role in platelet activation. The release of PDI from activated platelets was demonstrated nearly two decades ago and confirmed in many subsequent studies and it is also released by endothelial cells. Antibodies directed at PDI and micromolar concentrations of the antibiotic bacitracin inhibit platelet aggregation, adhesion, and secretion. Inhibition of PDI has been shown to inhibit cancer cell growth and induce tumor necrosis in an ovarian cancer model.

ERp5 is a 440 amino acid protein that contains two thioredoxin (CGHC containing motifs) domains and shares a 47% sequence identify with PDI. Blocking cell-surface ERp5 results in decreased platelet aggregation, fibrinogen binding, and alpha-granule secretion. In addition to its role in hemostasis, high levels of ERp5 expression have been shown to correlate with preventing an efficient antitumor response in Hodgkin lymphomas and have been proposed as a biomarker for prostate and breast cancer progression.

ERp57 is a thiol isomerase consisting of 505 amino acids and it plays important roles in regulating initial platelet activation and also supporting arterial thrombus formation, affecting platelet aggregation, dense granule secretion, fibrinogen binding, calcium mobilization and thrombus formation under arterial blood flow conditions. In addition to its role in thrombus formation, ERp57 has also been shown to be required for proper folding of influenza hemagglutinin and implicated in disease progression of Alzheimer's disease and cancer metastasis.

ERp72 is a 645 amino acid soluble ER protein which shares 37% sequence homology with PDI. ERp72 has three catalytic CGHC domains compared to the two found in PDI, ERp5 and ERp57. The percent increase of ERp72 recruited to the surface of platelets after activation is higher than that of PDI, ERp5 and ERp57, suggesting it performs an important albeit currently unknown role in platelet activation. The effect of ERp72 inhibition on thrombus formation is similarly unknown. In addition to its relocation to the activated platelet surface, ERp72 has been implicated in the infectious process of polyomavirus and also in the redox signaling of NADPH oxidase (Nox) 1.

In an embodiment, the target for inhibition is one or more thiol isomerases of the extracellular thiol isomerases, including protein disulfide isomerase (PDI), thioredoxin (TRX), ERp5, ERp57, and ERp72. In an embodiment, the target for inhibition is PDI. In an embodiment, the target for inhibition is thioredoxin (TRX). In an embodiment, the target for inhibition is ERp5. In an embodiment, the target for inhibition is ERp57. In an embodiment, the target for inhibition is ERp72.

The term "patient", as used herein, is a human or non-human animal in need of medical treatment. Medical treatment can include treatment of an existing condition, such as a disease or disorder, prophylactic or preventative treatment, or diagnostic treatment. In some embodiments the patient is a human patient.

The term "providing", as used herein, means giving, administering, selling, distributing, transferring (for profit or not), manufacturing, compounding, or dispensing.

The term "providing an extracellular thiol isomerase inhibitor compound or pharmaceutically acceptable salt thereof with at least one additional therapeutic agent", as used herein, means an extracellular thiol isomerase inhibitor compound or pharmaceutically acceptable salt thereof and the additional active agent(s) are provided simultaneously in a single dosage form, provided concomitantly in separate dosage forms, or provided in separate dosage forms for administration separated by some amount of time that is within the time in which both the extracellular thiol isomerase inhibitor compound or pharmaceutically acceptable salt thereof and the at least one additional active agent are within the blood stream of a patient. The extracellular thiol isomerase inhibitor compound or pharmaceutically acceptable salt thereof and the additional active agent need not be prescribed for a patient by the same medical care worker. The additional active agent or agents need not require a prescription. Administration of the extracellular thiol isomerase inhibitor compound or pharmaceutically acceptable salt thereof or the at least one additional active agent can occur via any appropriate route, for example, oral tablets, oral capsules, oral liquids, inhalation, injection, suppositories or topical contact.

The term "treatment", as used herein, includes providing an extracellular thiol isomerase inhibitor compound or pharmaceutically acceptable salt thereof, either as the only active agent or together with at least one additional active agent sufficient to: (a) prevent a disease or condition or a symptom of a disease or condition from occurring in a patient who may be predisposed to the disease or condition but has not yet been diagnosed as having it; (b) inhibiting the disease or condition, i.e. arresting its development; and (c) relieving the disease or condition, i.e., causing regression of the disease or condition. "Treating" and "treatment" also means providing a therapeutically effective amount of an extracellular thiol isomerase inhibitor compound or pharmaceutically acceptable salt thereof, as the only active agent or together with at least one additional active agent to a patient suffering from a disease or condition influenced by the activity of one or more extracellular thiol isomerases. "A disease or condition influenced by the activity of one or more extracellular thiol isomerases" means the one or more extracellular thiol isomerase is implicated in the disease or condition.

The extracellular thiol isomerase inhibitor compound or pharmaceutical compositions/combinations disclosed herein are useful for treating patients. The extracellular thiol isomerase inhibitor compound or pharmaceutical compositions/combinations are useful for treating or preventing diseases and disorders where the activity of one or more extracellular thiol isomerases are involved. In certain embodiments the patient is afflicted with thrombosis or is at a risk of developing a thrombosis. In certain embodiments the patient is afflicted with cancer. In certain embodiments the disease is hematological cancer, HPV associated cancer, ovarian cancer, prostate cancer, gastric cancer, breast cancer, or colorectal cancer. In other embodiments the patient to be treated is afflicted with an inflammatory disorder, an infectious disease, an immune disorder, or a neurologic disease.

Extracellular Thiol Isomerase Inhibitor Compounds

As used herein, "extracellular thiol isomerase inhibitor compound" is an inhibitor of one or more of the extracellular thiol isomerases. Exemplary extracellular thiol isomerase inhibitor compounds include zafirlukast, montelukast, CGP-13501 (CAS Reg. No. 56189-68-5), CGP-7930 (CAS Reg. No. 57717-80-3), alosetron, balsalazide, benserazide, butaclamol, leva-dopa, mesalazine, oxcarbazepine, a pharmaceutically acceptable salt, prodrug, and/or solid state form thereof. As inhibitors of one or more of the extracellular thiol isomerases, one or more of these compounds can be used as an anti-thrombotic agent, and anti-coagulant agent, an anti-inflammatory agent, an anti-viral agent, a chemotherapeutic or an anti-cancer agent, etc., or a combination thereof.

Zafirlukast is a synthetic, selective peptide leukotriene receptor antagonist (LTRA), with the chemical name 4-(5-cyclopentyloxycarbonylamino-1-methylindol-3-ylmethyl)-3-methoxy-N-o-tolylsulfonylbenzamide. We have found Zafirlukast to be a broad spectrum thiol isomerase inhibitor that inhibits platelet function, thrombus formation and cancer cell growth.

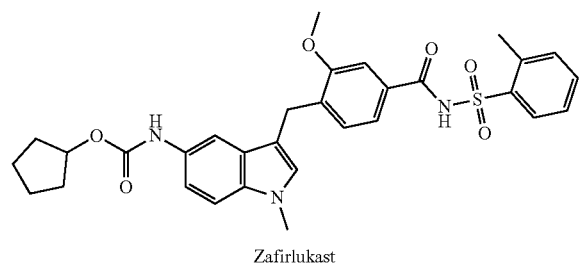 [SMILES: COc1cc(C(=O)NS(=O)(=O)c2ccccc2C)ccc1Cc1cn(C)c2ccc(NC(=O)OC3CCCC3)cc12]

Zafirlukast

The synthesis and pharmaceutical forms of zafirlukast are further described in U.S. Pat. Nos. 4,859,692; 5,294,636; 5,319,097; 5,482,963; 5,583,152; 5,612,367; 6,143,775; 6,333,361; and 6,399,104, the contents of which are incorporated herein by reference in their entireties.

Montelukast is a synthetic peptide leukotriene receptor antagonist (LTRA), with the chemical name [R-(E)]-1-[[[1-[3-[2-(7-chloro-2-quinolinyl)ethenyl]phenyl]-3-[2-(7-chloro-2-quinolinyl)ethenyl]phenyl]-3-[2-(1-hydroxy-1-methylethyl)phenyl]propyl]thio]methyl cyclopropane acetic acid. The synthesis and pharmaceutical forms of montelukast and montelukast sodium are further described in U.S. Pat. No. 5,565,473, which is incorporated herein by reference in its entirety.

The term "active agent", as used herein, means a compound (including the extracellular thiol isomerase inhibitor compound), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline (i.e. amorphous) forms, and any polymorphs of the compound are included. All forms are contemplated herein regardless of the methods used to obtain them.

The term "pharmaceutically acceptable salt", as used herein, includes derivatives of the disclosed compounds in which the parent compound is modified by making inorganic and organic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

Anti-Thrombotic

Extracellular thiol isomerases are involved the regulation of hemostasis and thrombosis, as the inhibition of one or more extracellular thiol isomerases will block platelet aggregation, granule secretion, adhesion, thrombus formation and fibrin generation. Antithrombotics can be used therapeutically for prevention (primary prevention, secondary prevention) or treatment of a dangerous blood clot (acute thrombosis).

Inhibiting the activity of PDI, ERp5 or ERp57 blocks thrombus formation following laser-induced injury of blood vessels in a murine model of thrombosis.

Furthermore, since inhibiting the activity of thiol isomerases effects both platelet accumulation and fibrin formation, these therapeutics would be an improvement over currently available therapies that only target either arterial clots (heart attacks and strokes largely triggered by inappropriate activation of platelets) or venous clots (deep-vein thrombosis and pulmonary embolism largely caused by inappropriate activation of the coagulation system). Data suggests that each thiol isomerase has unique substrate specificities and mechanisms of action suggesting each could be an independent target.

The thrombotic disease or condition to be prevented or treated by the extracellular thiol isomerase inhibitor compound can be acute myocardial infarction, stable angina, unstable angina, acute occlusion following coronary angioplasty and/or stent placement, a transient ischemic attack, cerebrovascular disease, stroke, peripheral vascular disease, placental insufficiency, atrial fibrillation, deep vein thrombosis, pulmonary embolism, or a combination thereof.

Platelet responses in the presence of zafirlukast, (0.1 µM-10 µM) were tested in a range of platelet functional assays including aggregation, granule secretion and spreading studies. Zafirlukast was found to inhibit platelet aggregation, dense and α-granule secretion, platelet spreading upon collagen and thrombus formation under flow. These data suggest that zafirlukast and other broad spectrum inhibitors of thiol isomerases of the protein disulfide isomerase subfamily can be used as an anti-thrombotic drug.

In an embodiment, the disease or condition influenced by the activity of one or more extracellular thiol isomerases is arterial thrombosis, venous thrombosis, a thrombotic disease such as acute myocardial infarction, stable angina, unstable angina, acute occlusion following coronary angioplasty and/or stent placement, a transient ischemic attack, cerebrovascular disease, stroke, peripheral vascular disease, placental insufficiency, atrial fibrillation, deep vein thrombosis, and pulmonary embolism, or a combination thereof; and wherein the extracellular thiol isomerase inhibitor compound is zafirlukast.

Anti-Cancer

PDI inhibition is a viable target for cancer therapy. See, Xu et al. "Protein disulfide isomerase: a promising target for cancer therapy" Drug Discovery Today, Vol. 19, No. 3, March 2014.

There is further evidence for tumor metastasis role for ERp5. See Gumireddy et al. "In vivo selection for metastasis promoting genes in the mouse" PNAS (2007) 104, 6696-6701.

ERp57 is expressed from the PDIA3 gene in humans. It consists of 505 amino acids and it is upregulated in breast, lung, uterine, stomach and hepatic cancer, as well as melanoma in comparison to normal tissues. The expression levels of ERp57 have been positively correlated with the transforming abilities of the oncogenic sarcoma virus in NIH3T3 cells, suggesting that ERp57 is involved in oncogenic transformation. Unlike the other PDI family members, ERp57 has the ability to interact with nuclear DNA and activate gene expression as ERp57 interacts with DNA molecules through its catalytically active a' domain. ERp57 is also a component of the STAT3-transcriptional complex and the ERp57-STAT3 modulates the cell signaling and proliferation regulated by STAT3. ERp57 also regulates gene expression through the mTOR pathway, which is another important regulator of cell proliferation and survival. ERp57 has also been implicated in binding at least three proteins involved with DNA repair, including Ref-1/APE, which itself has the ability to activate additional transcription factors. In addition to gene regulation functions, increased ERp57 expression is correlated to a resistance to treatment with paclitaxel in ovarian cancer and radioresistance in laryngeal cancer, promotes the metastasis of breast cancer into bone, and is involved in the deregulation of EGFR signaling in a breast cancer cell line, preventing its downstream activation of target molecules such as STAT3, Akt and PLCγ. As ERp57 plays a role in thrombus formation it is a potential target in the prevention of cancer-associated thrombosis, a major cause of morbidity and mortality in cancer patients.

The cancer to be treated with the extracellular thiol isomerase inhibitor compound can be ovarian, prostate, lung, melanoma, lymphoma, glioma, breast, or neuroblastoma.

The extracellular thiol isomerase inhibitor compound can be used alone or optionally in combination with another anti-cancer or chemotherapeutic agent.

In an embodiment, the cancer is treated with a combination of the extracellular thiol isomerase inhibitor compound and a chemotherapeutic agent such as carboplatin or cisplatin. In such an embodiment, the extracellular thiol isomerase inhibitor compound may provide an advantage by overcoming or preventing carboplatin and/or cisplatin resistance.

Anti-Infective/Anti-Viral

Thiol isomerases, in particular PDI, have also been implicated in HIV-1 entry. The use of a broad spectrum thiol isomerase inhibitor (e.g., zafirlukast) may offer protective effects to prevent virus entry as demonstrated by Khan et al. "Discovery of a Small Molecule PDI Inhibitor That Inhibits Reduction of HIV-1 Envelope Glycoprotein gp120." ACS Chemical Biology, Vol. 6, No. 3, March 2011.

The viral disease to be treated or prevented with the extracellular thiol isomerase inhibitor compound can be HIV, dengue virus, or rotavirus. The one or more extracellular thiol isomerase inhibitor compounds can further be used to treat or prevent infectious diseases such as cholera as demonstrated by Orlandi. "Protein Disulfide Isomerase-mediated Reduction of the A Subunit of Cholera Toxin in a Human Intestinal Cell Line." The Journal of Biochemistry, Vol. 272, No. 7 Feb. 14, 2007.

Anti-Inflammatory

The inflammation to be treated with the extracellular thiol isomerase inhibitor compound can be inflammation of the lungs, joints, connective tissue, eyes, nose, bowel, kidney, liver, skin, central nervous system, vascular system or heart. PDI has been demonstrated to play a critical role in the recruitment of neutrophils and activation of the innate immune response during vascular inflammation and tissue injury.

Neurologic and Neurodegenerative Disorders

Thiol isomerases are present in the brain and are upregulated in patients with neurological folding disorders such as Creutzfeldt-Jakob disease, Alzheimer's disease, Huntington's disease, and Parkinson's disease. The use of a broad spectrum thiol isomerase inhibitor (e.g., zafirlukast) may offer protective effects to prevent or reduce neurological degeneration, to treat neurodegenerative disorders, and treat neurologic diseases and disorders, due to the increased reactive oxygen species damage and apoptosis associated with PDI subfamily members in neurodegenerative diseases. Previous studies have demonstrated PDI inhibitors can suppress the toxicity associated with misfolded Huntingtin and b-amyloid proteins.

Pharmaceutical Compositions, Dosage

The one or more extracellular thiol isomerase inhibitor compounds can be administered as the neat chemical, or administered as a pharmaceutical composition. Accordingly, an embodiment provides pharmaceutical compositions comprising an extracellular thiol isomerase inhibitor compound or a pharmaceutically acceptable salt thereof, together with a pharmaceutically acceptable carrier. The pharmaceutical composition may contain an extracellular thiol isomerase inhibitor compound or pharmaceutically acceptable salt thereof as the only active agent, or may contain one or more additional active agents.

The extracellular thiol isomerase inhibitor compound may be administered orally, topically, parenterally, by inhalation or spray, sublingually, transdermally, via buccal administration, rectally, as an ophthalmic solution, or by other means, in dosage form containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, can be subdivided into suitably sized unit doses containing appropriate quantities of the active components, e.g., an effective amount to achieve the desired purpose.

The term "dosage form", as used herein, means a unit of administration of an active agent. Examples of dosage forms include tablets, capsules, injections, suspensions, liquids, emulsions, creams, ointments, suppositories, inhalable forms, transdermal forms, and the like. An exemplary dosage form is a solid oral dosage form.

The term "pharmaceutical compositions", as used herein, are compositions comprising at least one active agent, such as a compound or salt of Formula I, and at least one other substance, such as a carrier. Pharmaceutical compositions meet the U.S. FDA's GMP (good manufacturing practice) standards for human or non-human drugs. The pharmaceutical compositions can be formulated into a dosage form.

The term "carrier", as used herein, applied to pharmaceutical compositions refers to a diluent, excipient, or vehicle with which an active compound is provided.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the extracellular thiol isomerase inhibitor compound.

Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the extracellular thiol isomerase inhibitor compound.

The pharmaceutical compositions can be formulated for oral administration. These compositions contain between 0.1 and 99 weight percent ("wt. %") of the extracellular thiol isomerase inhibitor compound, specifically at least about 5 wt. %. In some embodiments, the composition contains from about 25 wt. % to about 50 wt. % or from about 5 wt. % to about 75 wt. % of the extracellular thiol isomerase inhibitor compound.

The term "therapeutically effective amount" of a pharmaceutical composition, as used herein, means an amount effective, when administered to a patient, to provide a therapeutic benefit such as a prevention or an amelioration of symptoms, e.g., to treat a patient suffering from a disease or condition influenced by the activity of one or more of the extracellular thiol isomerases. A therapeutically effective amount may vary according to factors such as the disease state, age, and weight of the patient, and the ability of the compound to elicit a desired response in the patient. Dosage regimens may be adjusted to provide the optimum therapeutic response. A therapeutically effective amount is also one in which any toxic or detrimental effects (e.g., side effects) of the inhibitor compound are outweighed by the therapeutically beneficial effects.

A therapeutically effective amount may range from about 0.001 µg/kg/day to about 500 mg/kg/day, preferably 0.01 µg/kg/day and 100 mg/kg/day. The skilled artisan will appreciate that certain factors may influence the dosage required to effectively treat a patient, including but not limited to the severity of the disease or disorder, previous treatments, the general health and/or age of the patient, and other diseases present. Moreover, treatment of a patient with a therapeutically effective amount of an inhibitor compound can include a single treatment or, can include a series of treatments. It will also be appreciated that the effective dosage of an inhibitor compound used for treatment may increase or decrease over the course of a particular treatment.

The extracellular thiol isomerase inhibitor compound can be administered once, twice, or three times a day to the patient in need thereof. Within this embodiment, the administration can be made orally.

When administered orally, the total daily dose zafirlukast, a pharmaceutically acceptable salt, prodrug, and/or a solid state form thereof, can be about 10 to about 200 mg, specifically about 20 to about 175 mg, more specifically about 40 to about 150 mg, and still more specifically about 60 to about 125 mg administered once, twice, or three times a day orally.

The pharmaceutical composition can be formulated in a package comprising the pharmaceutical composition in a container and further comprising instructions for using the composition in the prevention and treatment of a disease or disorder mediated by the one or more thiol isomerases of the extracellular thiol isomerases.

This invention is further illustrated by the following examples that should not be construed as limiting.

EXAMPLES

Example 1. Insulin-based Turbidometric Assay—Assay of Thiol Isomerase Inhibitory Activity Recombinant thiol isomerases were purchased from AbCam (Cambridge Mass.), recombinant insulin (bovine), bacitracin, dithiothreitol (DTT) buffers and all other chemicals were purchased from Sigma Aldrich (St. Louis, Mo.; while 384 well clear bottom plates were purchased from Corning (Corning, N.Y.).

The catalytic reduction of insulin by thiol isomerases in the presence of DTT results in aggregation of insulin chains. The turbidity of insulin aggregation can be monitored spectrophotometrically at an optical density (OD) at 650 nm. This approach has been used by multiple groups to identify thiol isomerase inhibitors in either a kinetic or endpoint fashion. A final concentration of either 10 µg/mL PDI, 30 µg/mL ERp5, 10 µg/mL ERp72 or 10 µg/mL thioredoxin, 125 µM insulin and 2 mM ethylenediaminetetraacetic acid (EDTA) in 30 µL of 100 mM potassium phosphate buffer was added to each experimental well plate, while negative control wells lacked any thiol isomerase. Lead compounds were diluted in a 6 point dose curve and the turbidity of insulin aggregation was measured kinetically each minute for 75 minutes using a Spectramax M3 plate reader (Molecular Devices, Sunnyvale, Calif.) Specificity assay utilized the insulin turbidity assay as well.

FIG. 1 illustrates the results of assay of thiol isomerase inhibitory activity of zafirlukast. Zafirlukast was found to be a broad inhibitor of PDI, ERp5, ERp57, ERp72, and thioredoxin (TRX) enzymes. Zafirlukast was found to have an inhibitory range on ERp5 of between 10-300 µM; PDI is inhibited between 30-300 µM; TRX is inhibited in the range of 10-300 µM; ERp57 is inhibited between 30-300 µM; and ERp72 is inhibited between 10-300 µM.

Figure 2:
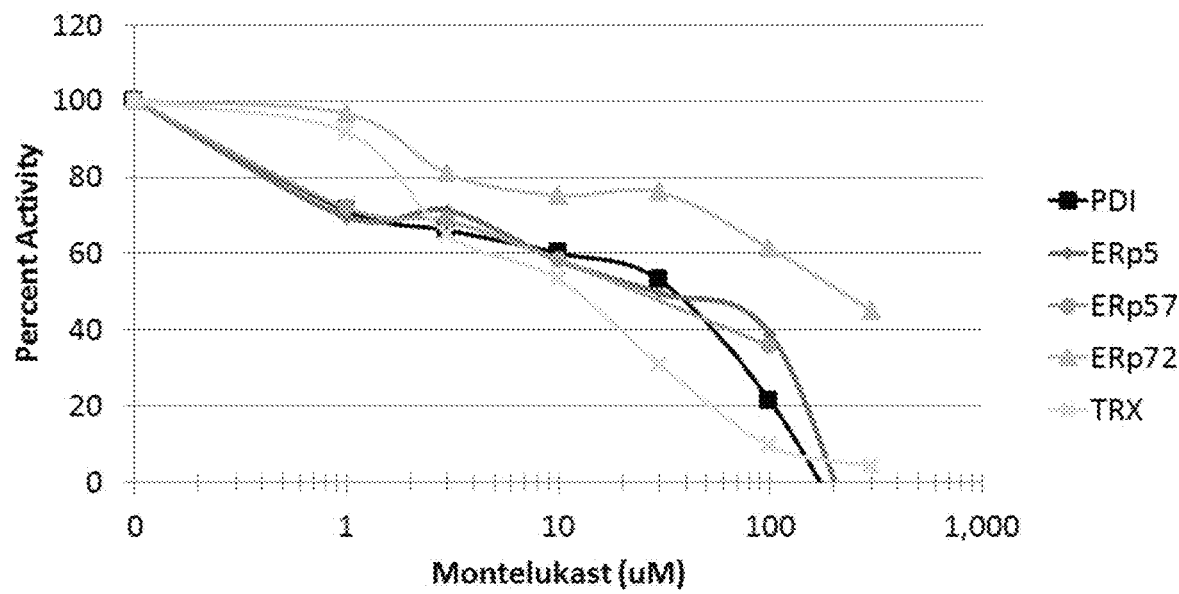
FIG. 2 illustrates data on the inhibition of various thiol isomerases by montelukast in an in vitro enzymatic assay.

FIG. 2 illustrates the results of assay of thiol isomerase inhibitory activity of montelukast.

Figure 3:
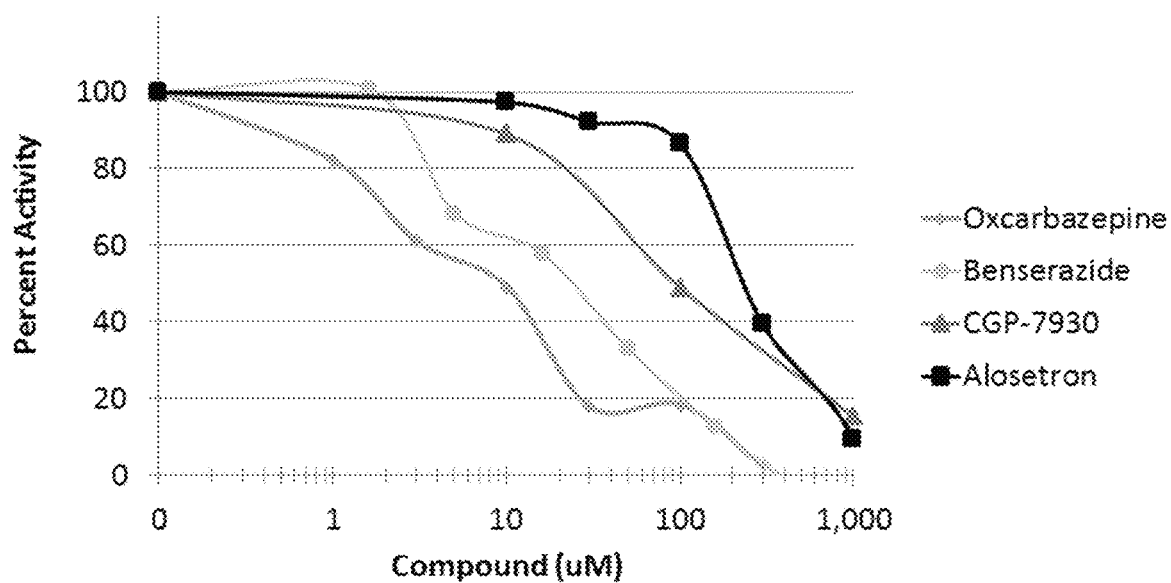
FIG. 3 illustrates data on the inhibition of ERp57 by other inhibitors at various concentrations in an in vitro enzymatic assay.

FIG. 3 illustrates data on the inhibition of ERp57 by inhibitors oxcarbazepine, benserazide, CGP-7930, and alosetron at various concentrations in an in vitro enzymatic assay. It was further found that CGP-13501 was specific for ERp57.

Example 2. Studies Showing Zafirlukast is a Thiol Isomerase Inhibitor that can Inhibit Platelet Function As zafirlukast and montelukast are broad spectrum inhibitor of thiol isomerases of the extracellular thiol isomerases (see Example 1), it would be expected to see a decreased overall platelet response when the platelets are treated with this compound.

Materials: Zafirlukast and montelukast were purchased from Sigma Aldrich (Poole, UK) Collagen was obtained from Takeda (Linz, Austria). Chronolume and ATP for dense granule secretion experiments were purchased from Chronolog (Pennsylvania, USA). Anti-human P-Selectin (CD62P) antibody and Anti-human PAC-1 antibody were obtained from BD Biosciences (New Jersey, USA) and anti-human fibrinogen FITC conjugate was obtained from Dako Cytochemicals (Cambridgeshire, UK). CRP-XL was purchased from Prof Richard Farndale (University of Cambridge, UK). Microscope slides and coverslips were purchased from VWR (Pennsylvania USA). Prolong Anti Fade Gold Medium and Alexa-Fluor Phalloidin 488 were obtained from Thermo Fisher (California, USA). Cellix chips were obtained from Cellix (Dublin, Ireland). DioC6, Thrombin, $PGI_2$, DMSO, Fibrinogen, Protease-free Bovine Serum Albumin (BSA) and all other reagents were of analytical grade and were obtained from Sigma Aldrich (Poole, UK).

Human Platelet Preparation: 50 mL of blood was drawn from drug free, consenting individuals, into a syringe containing 5 mL sodium citrate (4% w/v) and 7.5 mL warmed ACD (85 mM sodium citrate, 71 mM citric acid and 110 mM glucose). Blood was centrifuged at 102 g for 20 minutes to obtain platelet-rich plasma (PRP), which was then decanted and 104 prostacyclin ($PGI_2$ 125 µg/mL, solubilized in ethanol) added. Platelets were pelleted by centrifugation at 1413 g for 10 minutes, platelet poor plasma was discarded and the pellet resuspended in 25 mL Tyrode's-HEPES buffer (134 mM NaCl, 2.9 mM KCl, 0.34 mM $Na_2HPO_4$, 12 mM $NaHCO_3$, 20 mM HEPES, 1 mM $MgCl_2$ and 5 mM glucose pH 7.3), 3 mL of ACD and 10 µL $PGI_2$ were added and then following centrifugation at 1413 g for 10 minutes, the platelet pellet was re-suspended to the appropriate cell density using Tyrode's buffer. Platelets were rested for 30 minutes at 30° C. to allow platelet responses to recover.

Platelet Aggregation: 445 µL of washed platelets at ($4 \times 10^8$ cells/mL) were incubated for 5 minutes with vehicle (0.1% (v/v) DMSO) or 54 zafirlukast or montelukast. 50 µL of collagen 1 µg/mL (final), was added and light transmission monitored for 3 minutes at 37° C. with constant stirring (1200 rpm) using an aggregometer (Chronolog, USA).

Dense granule secretion: 395 µL of washed platelets were added to a cuvette and incubated with 5 µL of zafirlukast or vehicle (0.1% (v/v) DMSO) for 3 minutes at 37° C. 50 µL Chronolume substrate was added and incubated for a further 2 minutes. Platelets were then stimulated using 50 µL collagen (1 µg/mL) in a Lumi-aggregometer (Model 700, Chronolog USA) for 3 minutes at 37° C. with constant stirring (1200 rpm).

Thrombus Formation under flow: Human blood was drawn into 3.2% (w/v) sodium citrate and labelled with 2 µM DIOC-6 for an hour. A cellix biochip was coated with 1 µL Collagen (100 µg/mL) for 1 hour. Blood was then incubated with vehicle (0.1% (v/v) DMSO) or zafirlukast (10 µM) for 5 minutes prior to perfusion over collagen coated Cellix microfluidic cells at a shear rate of 20 dynes/$cm^2$. Images were recorded for 10 minutes perfusion by confocal microscopy (Nikon Al Microscope, Nikon, Japan) and analyzed using ImageJ.

Flow Cytometry: 5 µL platelets ($2 \times 10^8$ cells/mL) was added to 42 µL HEPES-buffered saline with 1 mM Ca2+. To this, 0.5 µL zafirlukast (0.6 µM-10 µM) or montelukast (0.6 µM-10 µM) or vehicle (0.1% (v/v) DMSO) was added and incubated for 5 minutes. 1 µL anti-human CD62p (1:500 dilution) and 1 µL anti-fibrinogen FITC conjugate (1:500 dilution) or 2 µL of anti-PAC-1 antibody were added to samples. Platelets were treated with 5 µL CRP-XL (1 ug/mL) or 5 µL Tyrode's for 20 minutes in the dark. Samples were then fixed with 450 µL of 0.2% (v/v) paraformaldehyde and analyzed on an accuri C6 flow cytometer (BD Biosciences, UK), with the threshold set to 20,000. Platelet populations were gated and 10,000 events recorded.

Statistical analyses: All raw data was analyzed by 1-way ANOVA and where appropriate normalized to vehicle. GraphPad Prism was used to perform statistical analysis by ANOVA or students T test. The level of significance of p values is as follows, *$p<0.05$, $p<0.01$, *$p<0.005$. Data presented are mean+/−standard error of the mean.

Zafirlukast inhibits platelet aggregation: Human washed platelets ($4 \times 10^8$ cells/mL) were pre-treated with 0.1 µM-10 µM zafirlukast or vehicle. Platelets were stimulated with collagen 1 µg/mL and allowed to aggregate for 3 minutes. Aggregation traces representative of the response were obtained and dose responses compared.

Figure 4:
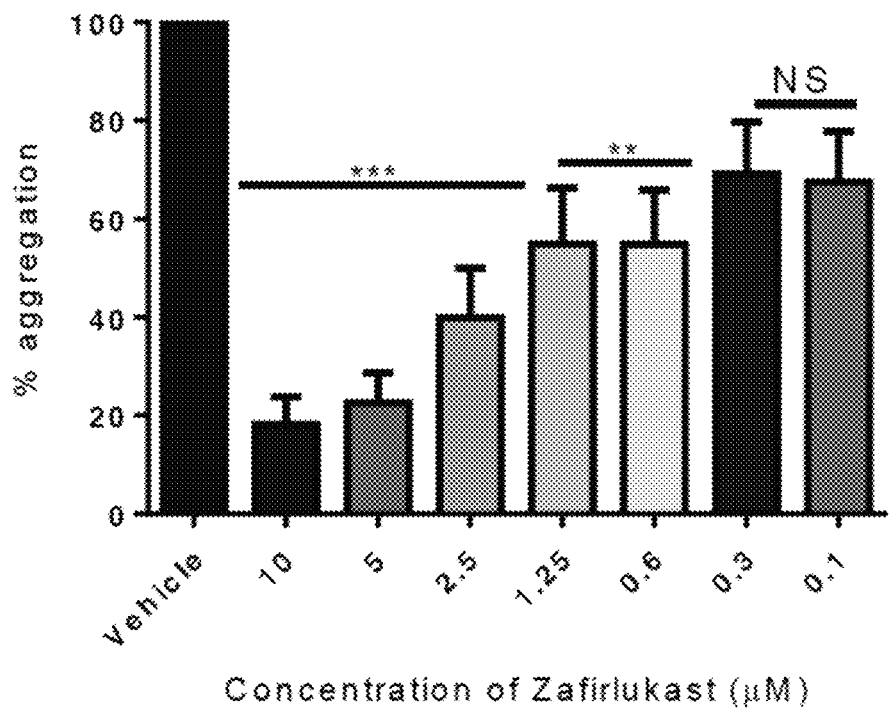
FIG. 4 illustrates data on the inhibition of collagen stimulated platelet aggregation by zafirlukast.

Data from 12 donors was normalized to vehicle and statistical significance was calculated using a one-way ANOVA against vehicle control. Zafirlukast was found to inhibit collagen stimulated platelet aggregation in a concentration dependent manner (FIG. 4). 10 µM Zafirlukast reduced platelet aggregation to 18.1% (±5.62%, 81.9% inhibition) ($p<0.0001$). 5 µM and 2.5 µM Zafirlukast inhibited platelet aggregation to 22.47%±6.2% and 40.00%±10.03% (77.53% and 60% inhibition respectively) ($p<0.0001$). Similar intermediate levels of aggregation were detected at concentrations 1.25 µM and 0.6 µM. The aggregation was 54.9% (±11.38%) and 54.8% (±11.07%) therefore 1.25 µM and 0.6 µM had a similar inhibition of 45%. ($p<0.01$). 0.3 µM and 0.1 µM did not significantly inhibit platelet aggregation. Montelukast was found to also inhibit collagen-stimulated platelet aggregation. 10 µM inhibited the aggregation response to 3.99±0.800%, 96.1% inhibition ($p<0.0001$). 5 µM, 3.75 µM and 2.5 µM which inhibited by 90.63%±3.14, 83.56%±10.35 and 62.13%±10.15 respectively and were all found to be statistically significant.

Zafirlukast inhibits dense granule secretion: The release of ATP and other molecules from dense granules contribute to the positive feedback mechanism and thus leads to a modification of the integrin αIIbβ3 and further aggregation of platelets. As platelet aggregation was disrupted by zafirlukast, the positive feedback action of granule exocytosis may also be disrupted.

Washed platelets ($4 \times 10^8$ cells/mL), were pre-treated with zafirlukast (0.1-10 µM) or vehicle for 3 minutes. Chronolume was added for a further 2 minutes before platelets were stimulated with 1 µg/mL (final) collagen in a lumi-aggregometer for 3 minutes. Statistical analysis was calculated using a one-way ANOVA (n=3), *$P<0.05$. Compared to vehicle secretion ATP (1.25 nM, ±0.34 nM), zafirlukast inhibited ATP secretion at 10 µM with mean ATP secretion being 0.327 nM (±0.0727 nM) ($P<0.05$).

Zafirlukast inhibits fibrinogen binding to αIIbβ3: Upon activation of platelets, the affinity of the fibrinogen receptor αIIbβ3 for its ligand, fibrinogen, increases. This allows crosslinking of platelets, allowing a thrombus to develop. PDI, ERp5 and ERp57 have all been shown to modulate fibrinogen binding through the use of function-blocking antibodies indicating a fundamental role for these enzymes in the affinity regulation in this receptor. The potential broad spectrum thiol isomerase inhibitor zafirlukast may also inhibit fibrinogen binding due to the inhibition of a granule secretion, in a similar fashion to the enzyme activity blocking antibodies.

The highest concentration of zafirlukast, 10 μM caused fibrinogen binding to be inhibited by 64.45% (±10.43%) (3696 Au±1159 Au) ($p<0.05$), compared to vehicle (12520 Au, ±3264). A trend towards inhibition was observed with lower concentrations of zafirlukast.

Zafirlukast inhibits integrin activation: After calcium release due to secondary messengers, the integrin αIIbβ3 undergoes a conformational change to form the active state and the anti-human PAC-1 antibody can bind.

Washed platelets ($2\times10^8$ cells/mL) were incubated with vehicle, zafirlukast (0.6-10 μM) or montelukast (0.6-10 μM) for 5 minutes. Following this, platelets were incubated with anti-PAC-1 antibody and stimulated with CRP-XL before levels of cell-surface bound PAC-1 antibody were examined by flow cytometry. Data were analyzed using one-way ANOVA, n=3.

Zafirlukast inhibited integrin activation at 10 μM by 54% (±4.337%, 748.5 Au, ±87.46,) when compared to vehicle (1623 Au, ±34.67) ($p<0.005$).

Zafirlukast affects thrombus formation under flow: It has been previously shown that thiol isomerases, in particular ERp57 play an important role in adhesion of platelets and formation of thrombi under arterial flow. An in vitro thrombus formation model was used to identify if zafirlukast has any physiological effects on thrombi formed under flow conditions.

Whole human blood labelled with the lipophilic dye DIOC-6 was incubated with zafirlukast (10 μM) or vehicle (0.1% (v/v) DMSO) for 5 minutes before perfusion over cellix capillaries coated with collagen (100 μg/mL) at an arterial shear rate of 20 dynes/cm$^2$. Images were recorded for 10 minutes using confocal microscopy and analyzed using ImageJ. The median fluorescence intensity was determined and compared to max intensity response; the more intense the fluorescence the larger the volume of thrombus formed.

For both the vehicle and zafirlukast treated blood, as the time increased the median fluorescence and therefore the size of the thrombus increased. After 8 minutes of flow, blood treated with 10 μM zafirlukast showed a slight decrease in median fluorescence intensity and therefore thrombus formation ($p<0.05$), MFI to 74.86 (±3.371 Au) compared to the vehicle at 89.15 (±1.679 Au). The final size of the thrombus also was significantly diminished compared to the vehicle ($p<0.05$; two way ANOVA, 3 donors). Zafirlukast inhibited the median fluorescence intensity by 14.25% compared to vehicle. It was therefore concluded that zafirlukast diminishes thrombus formation in whole blood under arterial flow conditions.

The foregoing results support the conclusion that zafirlukast inhibits platelet aggregation, granule secretion, integrin activation and thrombus formation under flow potentially through the mediation of thiol isomerases. These data support the potential of zafirlukast as a thiol isomerase inhibitor and inhibitor of platelet functional responses.

Figure 5:
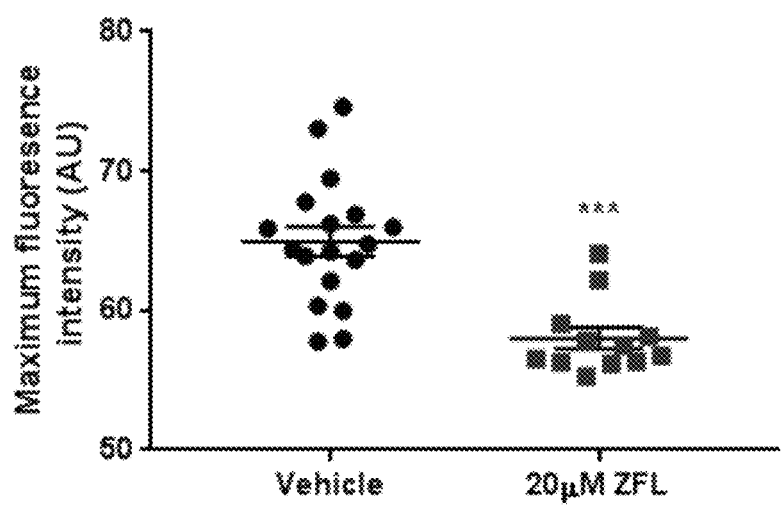
FIG. 5 illustrates the maximum fluorescence intensity of thrombi formed in mice in the presence of zafirlukast (squares) or vehicle (circles)
Figure 6:
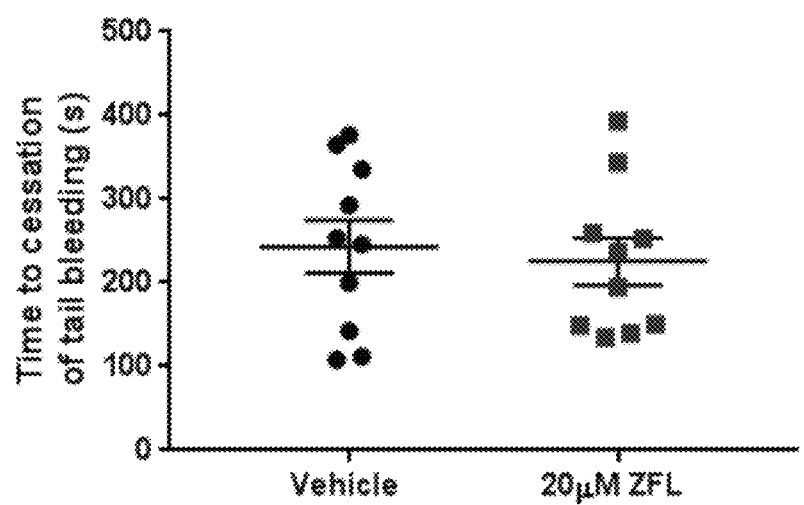
FIG. 6, effects of zafirlukast on bleeding time were assessed by tail bleeding assay.

Example 3. Zafirlukast Inhibits Thrombus Formation in Vivo but does not Impact on Bleeding in Mice The effects of zafirlukast on thrombus formation in mice was determined following laser injury of cremaster muscle arterioles, and observed by intravital microscopy. Male C57/BL6 mouse platelets were labelled with DyLight 649-conjugated anti-GPIb antibody (0.2 μg/g body weight) and either vehicle or zafirlukast (ZFL) infused (at a volume required to achieve a circulating concentration of 20 μM). Following laser injury, images were recorded for 5 minutes. FIG. 5 illustrates the maximum fluorescence intensity of each thrombus formed in vehicle treated mice (n=18 thrombi, circles) or ZFL treated mice (n=12 thrombi, squares) and demonstrates that treatment with ZFL results in a reduction in thrombus size. FIG. 6 illustrates the effects of ZFL on bleeding were determined by tail bleeding assay. Vehicle or ZFL (at a volume required to achieve a circulating concentration of 20 μM) were infused into the femoral veins of C57/BL6 mice, 5 minutes prior to tail biopsy. 0.5 cm of tail tip was excised and blood collected in phosphate-buffered saline (PBS), and time to cessation of bleeding was recorded. Treatment with ZFL was associated with no change in bleeding time. Graphs represent mean±SEM, n=10 per treatment, data analyzed by Student's T test, ***$p<0.005$.

Example 4. Effects of Extracellular Thiol Isomerase Inhibitors on Cancer Cell Growth Cells were plated at 6,000 cells/well in a 96-well plate and treated with the indicated concentration of zafirlukast 24 hours later. Cells were allowed to grow for an additional 24 hours before alterations in growth were measured by the PrestoBlue cell proliferation assay in triplicate. Fluorescence readings with an excitation at 570 nm and emission of 600 nm were collected and treated samples were converted to a percentage of the untreated controls.

OVCar8 (human ovarian cancer cell line), HCT116 (human colon cancer), HeLa (cervical cancer cell line) and MDA-MB-231 (breast cancer cell line) cell lines were examined for their ability to inhibit cell proliferation. OVCar8 and HCT116 cells exhibited an IC50 in the 5-10 μM range. HeLa cervical cancer cells and MDA-MB-231 breast cancer cell lines were less sensitive. Table 1 illustrates the results of a cell proliferation assay testing zafirlukast against OVCar8 cells, HCT116 cells, HeLa cells and MDA-MB-231 cells.

TABLE 1

| Cell Line | Tumor Type | IC$_{50}$ |
| --- | --- | --- |
| HCT116 | Colon Cancer | 5 μM (±2 μM) |
| OVCar8 | Ovarian Cancer | 6 μM (±2 μM) |
| HeLa | Cervical Cancer | 30 μM (±5 μM) |
| MDA-MB-231 | Breast Cancer | 100 μM (±7 μM) |

Example 5. Zafirlukast Inhibits EGFR Signaling

HCT116 (human colon cancer) cells were incubated with drug for 24 hours and total cellular extracts prepared. Protein levels were normalized, protein loaded on SDS-polyacrylamide gels and then electrophoresed before transferring to a PVDF membrane. The membranes were probed with primary antibodies of interest, followed by secondary antibodies conjugated with horseradish peroxidase. Western blot of HCT116 cells treated with zafirlukast showed almost complete inhibition of EGFR activation and its downstream signaling, monitored through measurement of STAT3 phosphorylation.

Unless defined otherwise, technical and scientific terms used herein have the same meaning as is commonly understood by one of skill in the art to which this disclosure belongs.

The singular forms "a," "an," and "the" include plural referents unless the context clearly dictates otherwise. The endpoints of all ranges directed to the same characteristic or component are independently combinable and inclusive of the recited endpoint. The suffix "(s)" as used herein is intended to include both the singular and the plural of the term that it modifies, thereby including one or more of that term (e.g., the carrier(s) includes one or more carriers). The term "or" means "and/or" unless clearly indicated otherwise by context. The term "combination" is inclusive of blends, mixtures, and the like.

Reference throughout the specification to "an embodiment", "another embodiment", "some embodiments", and so forth, means that a particular element (e.g., feature, structure, step, or characteristic) described in connection with the embodiment is included in at least one embodiment described herein, and may or may not be present in other embodiments. In addition, it is to be understood that the described elements may be combined in any suitable manner in the various embodiments.

In general, the compositions, methods, and articles can alternatively comprise, consist of, or consist essentially of, any ingredients, steps, or components herein disclosed. The compositions, methods, and articles can additionally, or alternatively, be formulated, conducted, or manufactured so as to be devoid, or substantially free, of any ingredients, steps, or components not necessary to the achievement of the function or objectives of the present claims.

"Optional" or "optionally" means that the subsequently described event or circumstance may or may not occur, and that the description includes instances where the event occurs and instances where it does not.

"About" or "approximately" as used herein is inclusive of the stated value and means within an acceptable range of deviation for the particular value as determined by one of ordinary skill in the art, considering the measurement in question and the error associated with measurement of the particular quantity (e.g., the limitations of the measurement system). For example, "about" can mean within one or more standard deviations.

While the invention has been described in detail in connection with only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Additionally, while various embodiments of the invention have been described, it is to be understood that aspects of the invention can include only some of the described embodiments. Accordingly, the invention is not to be seen as limited by the foregoing description, but is only limited by the scope of the appended claims.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

The invention claimed is:

1. A method, comprising:
    administering to a patient in need thereof a therapeutically effective amount of an extracellular thiol isomerase inhibitor compound to treat a disease or condition that is thrombosis or a thrombotic disease, wherein the extracellular thiol isomerase inhibitor compound is zafirlukast or a pharmaceutically acceptable salt thereof; and further comprising providing the patient with at least one additional therapeutic agent.

2. The method of claim 1, wherein the extracellular thiol isomerase is protein disulfide isomerase (PDI), thioredoxin, ERp5, ERp57, ERp72, or a combination thereof.

3. The method of claim 1, wherein the thrombotic disease is acute myocardial infarction, stable angina, unstable angina, acute occlusion following coronary angioplasty and/or stent placement, a transient ischemic attack, cerebrovascular disease, stroke, peripheral vascular disease, placental insufficiency, atrial fibrillation, deep vein thrombosis, pulmonary embolism, or a combination thereof.

4. The method of claim 1, wherein the extracellular thiol isomerase inhibitor compound is formulated as a pharmaceutical composition optionally further comprising a pharmaceutically acceptable carrier.

5. The method of claim 1, wherein the extracellular thiol isomerase inhibitor compound is formulated as a pharmaceutical composition in dosage form.

6. The method of claim 5, wherein the extracellular thiol isomerase inhibitor compound is formulated as a tablet or capsule.

7. The method of claim 1, wherein the extracellular thiol isomerase inhibitor compound is formulated as a pharmaceutical composition suitable for administration orally, topically, parenterally, by inhalation or spray, sublingually, transdermally, via buccal administration, or rectally.

8. The method of claim 1, wherein the additional therapeutic agent is an anti-thrombotic, an anti-coagulant, a chemotherapeutic, an anti-viral, or an anti-inflammatory.

9. A method for treating thrombosis, a thrombotic disease, platelet aggregation, fibrin generation, or a combination thereof in a patient, comprising:
    administering to the patient in need thereof a therapeutically effective amount of zafirlukast.

10. The method of claim 9, for the treatment of arterial thrombosis and venous thrombosis.

11. The method of claim 9, comprising administering a total daily dose of zafirlukast of about 10 to about 200 mg.

* * * * *